United States Patent [19]

Siegel

[11] 4,261,200

[45] Apr. 14, 1981

[54] SEMI-PERMEABLE PSYCHROMETRIC HYGROMETER

[76] Inventor: Israel Siegel, 351 W. 71 St., New York, N.Y. 10023

[21] Appl. No.: 89,218

[22] Filed: Oct. 29, 1979

[51] Int. Cl.³ ............................................. G01W 1/06
[52] U.S. Cl. .................................................. 73/338
[58] Field of Search ...................... 73/338.6, 338, 338.3

[56] References Cited

U.S. PATENT DOCUMENTS

| 1,586,351 | 5/1926 | Bristol et al. | 73/338 |
| 1,632,729 | 6/1927 | Foote et al. | 73/338 |

Primary Examiner—Donald O. Woodiel

[57] ABSTRACT

An improved psychrometric hygrometer obtains its wet-bulb temperature without surface water of induced air flow, through evaporation from transparent semi-permeable containers of relatively large surface-volume ratio.

5 Claims, 1 Drawing Figure

SEMI-PERMEABLE PSYCHROMETRIC HYGROMETER

BACKGROUND AND OBJECTIVES

The invention relates to means for measuring the relative humidity and in particular to improvements in psychrometric hygrometers.

Psychrometric hygrometers are the most common means for the determination of relative humidities. The relative humidity is derived from the difference between the dry-bulb and web-bulb temperatures. In currently available psychrometric hygrometers the wet-bulb temperature is obtained by the evaporation of a thin layer of water from a thermometer bulb. This requires means such as wicks for spreading a thin layer of water over a thermometer bulb. In addition, means are required to induce air movements around the wet-bulb. This requires fans or blowers, or rapid movements of the wet thermometer through the surrounding air. The present invention consists of a psychrometric hygrometer which provides a wet-bulb temperature without means for spreading surface water and without induced air movements. It utilizes the evaporation of water from a semi-permeable container rather than from surface water layers. A relatively large surface-volume container ratio induces a wet-bulb temperature without induced air movements. A detailed description of the invention is given in the Detailed Description section.

FIG. 1 is a front cross-sectional view of the invention.

DETAILED DESCRIPTION

Figure 1:
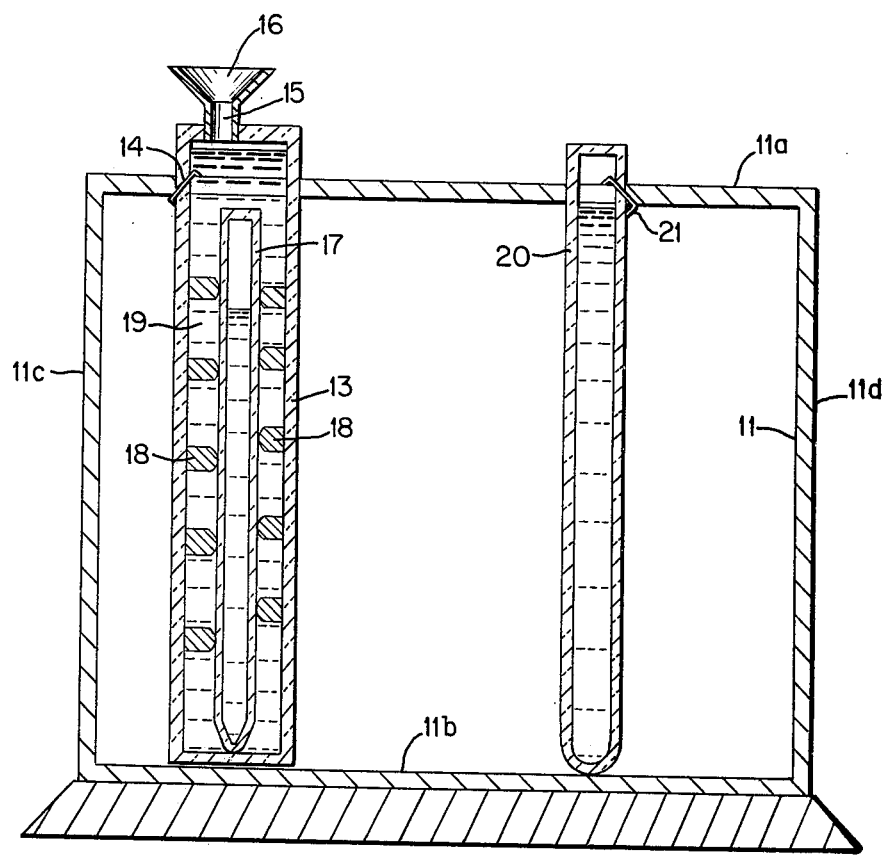

As shown in FIG. 1 there is present an open frame 11 consisting of two horizontal bars 11a and 11b, and two vertical bars 11c and 11d. The bars 11c and 11d are kept in a vertical position through a relative wide base 12, attached to the bottom horizontal bar 11b. A semi-permeable tube 13 is attached to frame 11 by wires 14. The arrangement is that tube 13 forms a 90° angle with the horizontal bars 11a and 11b. The tube 13 is made out of a transparent semi-permeable material such as unshrunk Vykor glass (Corning). The glass is permeable to water vapor but not to liquid water. The tube 13 is closed at both ends except for a small opening 15 in the top wall of tube 13. Attached to opening 15 is a small funnel 16. The relative dimensions of tube 13 are such that a surface volume ratio of at least 2 is obtained. This relatively large ratio increases the amount of water evaporating per unit volume of the water as will be described.

Present inside tube 13 is a thermometer 17. Flexible guiding knobs 18 protrude into the inside of tubes 13 from the inside walls of tube 13. The knobs 18 push against thermometer 17 and prevent it from moving in the tube 13. The tube 13 is filled with water 19. The water is transferred to the tube 13 from a water source (not shown) through funnel 16 and opening 15.

Present adjacent to tube 13 is a second thermometer 20. The thermometer 20 is attached to frame 11 by wires 21.

The operation of the hygrometer is as follows. Tube 14 is filled with water 19 through funnel 16 and opening 15. The water 19 evaporates through the porous walls of the tube 14. This cools the water 19 to its wet-bulb temperature. The cold water cools the immersed thermometer 17. The wet-bulb temperature is read in the thermometer 17 through the transparent walls of tube 14. The dry-bulb temperature is read in the adjacent thermometer 21. The difference between the wet and dry-bulb temperature is used to calculate the relative humidity from standard hygrometric charts.

While the invention has been described with reference to the embodiment of FIG. 1, it will be readily understood that modification in certain details may be made without departing from the essence of the invention as described in the Claims.

What is claimed:

1. A hygrometer comprising a container,
   at least a portion of said container having semi-permeable walls, said walls being permeable to water vapor but relatively impermeable to liquid water,
   water in said container evaporating from said semi-permeable walls,
   a large surface-volume ratio of said container to obtain a wet-bulb temperature without induced air flow, and
   means to indicate the temperature of said water.

2. The invention as described in claim 1 wherein said semi-permeable walls are transparent.

3. The invention as described in claim 1 wherein said means to indicate the temperature consist of a thermometer immersed in said water.

4. The invention as described in claim 1 and including an open frame to hold said container.

5. The invention as described in claim 4 and including a second thermometer outside of said container, attached to said frame to indicate the dry-bulb temperature.

* * * * *